US012017013B2

(12) United States Patent
Sasamine et al.

(10) Patent No.: US 12,017,013 B2
(45) Date of Patent: Jun. 25, 2024

(54) CATHETER SHAFT WITH MULTIPLE WIRE REINFORCEMENT AND ASSOCIATED DEVICES, SYSTEMS, AND METHODS

(71) Applicant: PHILIPS IMAGE GUIDED THERAPY CORPORATION, San Diego, CA (US)

(72) Inventors: Kazuo Sasamine, Lemon Grove, CA (US); Christopher Leblanc, Carlsbad, CA (US); Derek Rissman, San Diego, CA (US); Richard Bamberg, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 739 days.

(21) Appl. No.: 16/747,128

(22) Filed: Jan. 20, 2020

(65) Prior Publication Data

US 2021/0220607 A1 Jul. 22, 2021

(51) Int. Cl.
*A61M 25/01* (2006.01)
*A61M 25/00* (2006.01)
*A61M 25/09* (2006.01)

(52) U.S. Cl.
CPC . *A61M 25/0105* (2013.01); *A61M 2025/0002* (2013.01); *A61M 2025/0063* (2013.01); *A61M 2025/09116* (2013.01); *A61M 2025/09133* (2013.01); *A61M 2025/09191* (2013.01)

(58) Field of Classification Search
CPC ...... A61M 25/0105; A61M 2025/0002; A61M 2025/0059; A61M 2025/0063; A61M 2025/09116; A61M 2025/09133; A61M 2025/09191; A61M 25/005; A61M 25/0012; A61M 25/0053
See application file for complete search history.

(56) References Cited

U.S. PATENT DOCUMENTS

| 10,071,222 | B2* | 9/2018 | Leeflang | A61M 25/0012 |
| 10,426,920 | B2* | 10/2019 | Sutermeister | A61M 25/005 |
| 10,493,234 | B2* | 12/2019 | Kanazawa | A61M 25/005 |
| 2005/0182319 | A1* | 8/2005 | Glossop | A61B 8/481 600/424 |
| 2009/0163818 | A1* | 6/2009 | Zelenka | A61M 25/0054 600/467 |
| 2010/0094258 | A1 | 4/2010 | Shimogami | |
| 2014/0276074 | A1* | 9/2014 | Warner | D07B 1/0693 600/459 |
| 2015/0174363 | A1 | 6/2015 | Sutermeister | |
| 2017/0252535 | A1* | 9/2017 | Ganske | A61M 25/0041 |

(Continued)

FOREIGN PATENT DOCUMENTS

CN 105982733 A 10/2016

*Primary Examiner* — Devin B Henson

(57) ABSTRACT

Disclosed is an intraluminal catheter that includes a flexible elongate shaft configured to be positioned within a body lumen of a patient, and an intraluminal sensor disposed at the distal portion of the shaft that is configured to sense a characteristic within the body lumen. The shaft further comprises a plurality of wires disposed around a lumen, wherein the wires are helically twisted. The wires can be helically twisted in a single direction to form a cylindrical shape. This helical structure is configured to stiffen the flexible elongate shaft for movement into an obstruction within the body lumen without kinking.

17 Claims, 12 Drawing Sheets

(56) References Cited

U.S. PATENT DOCUMENTS

| | | |
|---|---|---|
| 2018/0093087 A1 | 4/2018 | Beach |
| 2019/0224447 A1 | 7/2019 | Ranum |
| 2019/0321059 A1 | 10/2019 | Takahashi |

* cited by examiner

CATHETER SHAFT WITH MULTIPLE WIRE REINFORCEMENT AND ASSOCIATED DEVICES, SYSTEMS, AND METHODS

TECHNICAL FIELD

The subject matter described herein relates to a device for intraluminal insertion, sensing and treatment within a body. This device has particular but not exclusive utility for intravascular imaging and treatment in highly occluded blood vessels.

BACKGROUND

Catheters on the market today are low cost products whose design is driven by the needs of manufacturers. Catheters are not typically designed to serve multiple functions, and many have features that prevent or limit their use for certain applications. Most devices on the market are built with polymer-based materials, which may not promote enough strength within the catheter body to enable sufficient simultaneous pushability, torqueability, trackability and flexibility to enable maneuvering through highly occluded vessels. Issues occur with these products because they don't have the performance attributes (torque, push, etc.) required to diagnose and treat chronic total occlusion cases, highly stenosed vessels, etc. The device needs to have torqueability and pushability in order to get through the cap of a chronic total occlusion (CTO) without kinking, buckling, twisting, or bulging. Additionally, if the device goes sub-intimal (e.g., leaves the true lumen of the blood vessel and is pushed between the intima and media of the vessel wall, where resistance may be lower), whether deliberately or accidentally, the catheter needs to exhibit 1:1 torque between the proximal and distal ends, so the clinician can maneuver the catheter back into the true lumen of the blood vessel.

Some catheters have a metal mesh within the catheter wall, but these meshes are not welded or otherwise self-attached, and are supported only by a surrounding polymer matrix. This may not add sufficient strength for the clinical applications described above.

The information included in this Background section of the specification, including any references cited herein and any description or discussion thereof, is included for technical reference purposes only and is not to be regarded as subject matter by which the scope of the disclosure is to be bound.

SUMMARY

Disclosed is a catheter shaft body that incorporates multiple metal wires of different sizes and/or shapes, arranged in a spiral configuration and welded or otherwise joined or coupled at the ends. The present disclosure provides a unique shaft body design for a multipurpose catheter for diagnostic and/or therapeutic use, for example in diagnosis or treatment of diseases of coronary or peripheral blood vessels. The catheter is constructed with multiple metal wires that are wound next to each other in a single spiral direction or chirality. Individual metal wires may have different sizes and/or shapes, such that differently sized and/or shaped metal wires are wound next to each other. This invention overcomes the limitations of the related art and advantageously promotes an increase in flexibility, torqueability, pushability, trackability, CTO crossing and sub-intimal entry and exit. The catheter shaft body disclosed herein has particular, but not exclusive, utility for diagnosis and treatment of vascular diseases in highly occluded blood vessels.

One general aspect of the intraluminal catheter includes a flexible elongate shaft configured to be positioned within a body lumen of a patient, where the flexible elongate shaft includes a proximal portion and a distal portion; and an intraluminal sensor disposed at the distal portion and configured to sense a characteristic associated with the body lumen while positioned within the body lumen, where the flexible elongate shaft further includes a lumen and a plurality of wires disposed around the lumen, where the plurality of wires is helically twisted.

Implementations may include one or more of the following features. The intraluminal catheter where the plurality of wires is helically twisted in a single direction to form a cylindrical shape. The intraluminal catheter where the plurality of wires is configured to stiffen the flexible elongate shaft for movement into an obstruction within the body lumen without kinking. The intraluminal catheter where the plurality of wires extends from the proximal portion of the flexible elongate shaft to the distal portion of the flexible elongate shaft. The intraluminal catheter where the plurality of wires includes a proximal portion and a distal portion, where the cylindrical shape is open at the proximal portion of the plurality of wires and the distal portion of the plurality of wires. The intraluminal catheter where the plurality of wires includes a proximal portion and a distal portion, where the plurality of wires is coupled only at the proximal portion of the plurality of wires and the distal portion of the plurality of wires. The intraluminal catheter where the flexible elongate shaft further includes a plurality of lumens, where the lumen is one of the plurality of lumens, where the plurality of wires is disposed around the plurality of lumens. The intraluminal catheter where the plurality of wires includes a pitch associated with the helical twist, where a larger pitch corresponds to an increased stiffness and decreased flexibility of the flexible elongate shaft and a smaller pitch corresponds to a decreased stiffness and increased flexibility of the flexible elongate shaft. The intraluminal catheter where the plurality of wires includes wires of different sizes and/or wires of different shapes. The intraluminal catheter where the plurality of wires is adjacent to one another to form the cylindrical shape. The intraluminal catheter where the plurality of wires includes wires of different cross-sectional areas and/or wires of different cross-sectional shapes. The intraluminal catheter where the plurality of wires includes an inner profile and an outer profile, where at least one of the inner profile or the outer profile is varying. The intraluminal catheter where the plurality of wires includes an inner profile and an outer profile, where at least one of the inner profile or the outer profile is constant. The intraluminal catheter where the plurality of wires is arranged in a first layer and a second layer disposed around the first layer. The intraluminal catheter where wires of the first layer are helically twisted in a first direction and wires of the second layer are helically twisted in an opposite, second direction. The intraluminal catheter where the flexible elongate shaft further includes an inner polymer layer, where the plurality of wires is positioned around the inner polymer layer. The intraluminal catheter where the flexible elongate shaft further includes an outer polymer layer, where the outer polymer layer is positioned around the plurality of wires. The intraluminal catheter further including a retractable needle disposed at the distal portion of the flexible elongate shaft. The intraluminal catheter where the intraluminal sensor includes at least of an intravascular ultrasound (IVUS) transducer, a pressure sensor, a flow sensor, or a temperature sensor.

One general aspect includes an intravascular catheter. The intravascular catheter also includes a flexible elongate shaft configured to be positioned within a blood vessel of a patient, where the flexible elongate shaft includes a proximal portion and a distal portion; and an intravascular sensor disposed at the distal portion and configured to sense a characteristic associated with the blood vessel while positioned within the blood vessel, where the intravascular sensor includes at least of an intravascular ultrasound (IVUS) transducer, a pressure sensor, a flow sensor, or a temperature sensor, where the flexible elongate shaft further includes a lumen and a plurality of wires disposed around the lumen, where the plurality of wires extends from the proximal portion of the flexible elongate shaft to the distal portion of the flexible elongate shaft, where the plurality of wires is helically twisted in a single direction to form a cylindrical shape, where the plurality of wires includes wires of different cross-sectional areas and/or wires of different cross-sectional shapes, where the plurality of wires is adjacent to one another to form the cylindrical shape, and where the plurality of the wires is configured to stiffen the flexible elongate member for movement into an obstruction within the blood vessel without kinking.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the catheter shaft body, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
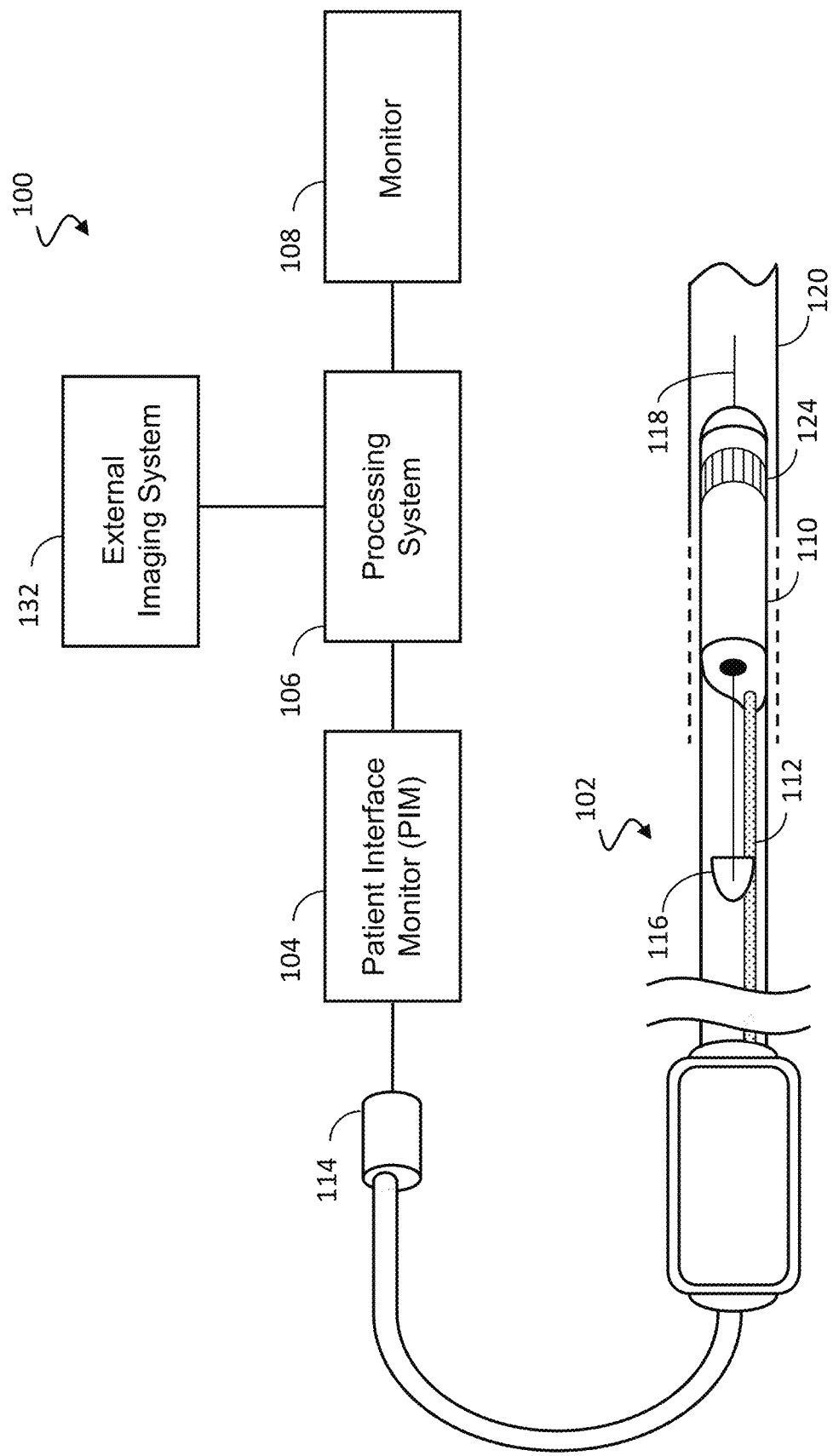
FIG. 1 is a diagrammatic schematic view of an intraluminal imaging, measurement, or treatment system, according to aspects of the present disclosure.

In accordance with at least one embodiment of the present disclosure, a flexible, elongate catheter shaft body is provided which incorporates multiple metal wires of different sizes and/or shapes, arranged in a spiral configuration and welded or otherwise coupled at the ends. The present disclosure provides a unique shaft body design for a multi-purpose catheter for diagnostic and/or therapeutic use, for example, in percutaneous transluminal coronary angioplasty (PTCA), percutaneous transluminal angioplasty (PTA), intravascular imaging (e.g., IVUS imaging), intravascular pressure measurements, flow measurements, or temperature measurements, and various forms of contact and noncontact therapy on coronary or peripheral vessels of the human body. The catheter is constructed with multiple metal wires having different sizes and/or shapes, such that differently sized and/or shaped metal wires are wound next to each other in a single spiral direction or chirality. This unconventional design overcomes the limitations of the related art and advantageously improves flexibility, torqueability, pushability, and trackability of the catheter shaft, for improved CTO crossing, including improved sub-intimal entry and exit capabilities.

The present disclosure aids substantially in intravascular diagnostic and treatment procedures, by preserving flexibility of the catheter shaft while reducing its tendency to kink, buckle, twist, or bulge. The catheter shaft body disclosed herein provides 1:1 torque, such that rotation at the proximal end of the catheter shaft is matched by an equal rotation at the distal end, regardless of resistance encountered within the vessel. The catheter shaft body also provides 1:1 translation, such that pushing or pulling on the proximal end of the catheter shaft results in equal pushing or pulling force and movement at the distal end, without kinking, buckling, or bulging, regardless of resistance encountered within the vessel. This improved design transforms difficult procedures such as subintimal catheterization followed by a return to the true lumen, which may currently have a success rate of less than 50%, into routine procedures with near 100% success rates. This unconventional approach improves the functioning of imaging and treatment systems for intraluminal insertion, by providing a catheter body that can be reliably pushed, pulled, and twisted through, past, around, and beyond an obstruction (including but not limited to an occlusion, total occlusions, chronic total occlusion, plaque, calcified plaque, thrombus, constriction, compression, or other stenosis).

These descriptions are provided for exemplary purposes only, and should not be considered to limit the scope of the catheter shaft body. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging, measurement, or treatment system, according to aspects of the present disclosure. The intraluminal imaging measurement, or treatment system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging, measurement, or treatment system 100 (or intravascular imaging, measurement, or treatment system) can be any type of imaging system suitable for use in the lumens or vasculature of a patient. In some embodiments, the intraluminal imaging, measurement, or treatment system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities. In still other embodiments, the system may comprise non-imaging sensors including but not limited to pressure, flow, or temperature sensors, or may include treatment subsystems including but not limited to noncompliant balloons, RF or ultrasound heating elements, etc.

It is understood that the system 100 and/or device 102 can be configured to obtain any suitable intraluminal data. In some embodiments, the device 102 may include an imaging component of any suitable imaging modality, such as optical imaging, optical coherence tomography (OCT), etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System (HIS) via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 may receive echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as a post-stent inspection to determine the status of a stent that has been positioned in a lumen.

The external imaging system 132 can be configured to obtain x-ray, radiographic, angiographic (e.g., with contrast), and/or fluoroscopic (e.g., without contrast) images of the body of a patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Before continuing, it should be noted that the examples described above are provided for purposes of illustration, and are not intended to be limiting. Other devices and/or device configurations may be utilized to carry out the operations described herein.

Figure 2:
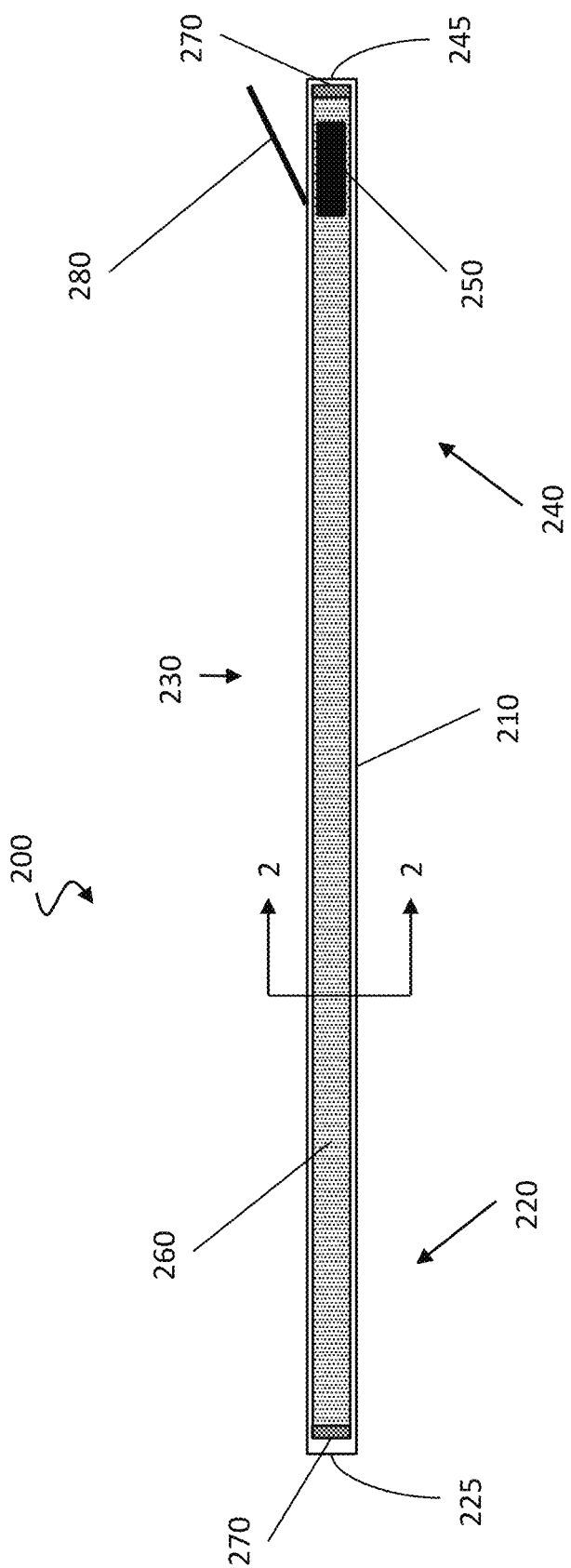
FIG. 2 is a diagrammatic top view of an intravascular device sized and shaped for insertion into vasculature of a patient, in accordance with at least one embodiment of the present disclosure.

FIG. 2 is a schematic or diagrammatic view of an intravascular device 200 sized and shaped for insertion into vasculature (e.g., a blood vessel) of patient, in accordance with at least one embodiment of the present disclosure. For example, the device can be inserted into and/or positioned within an artery, vein, aorta, chamber of the heart, and/or other suitable regions of the body of the patient. The intravascular device 200 can be a catheter, guide catheter, or a guide wire. The intravascular device can include a flexible elongate member or shaft 210 having a proximal portion 220 that terminates at a proximal end 225, a distal portion 240 that terminates at a distal end 245, and a central portion 230 extending between the proximal portion 220 and the distal portion 240. The intravascular device 200 can include one or more working elements 250, such as sensor(s) and/or therapy device(s). While one working element 250 is shown, it should be understood the intravascular device can include two or more working elements 250. For example, the working element can be an imaging device (e.g., intravascular ultrasound (IVUS), optical coherence tomography (OCT), forward-looking IVUS (FLIVUS), intra-cardiac echo (ICE)), pressure sensor, flow sensor, temperature sensor, electrophysiology (EP) device, balloon (e.g., angioplasty balloon, drug-coated balloon), atherectomy device, stent, delivery device (e.g., stent, drug), laser device, ablation device (e.g., radio frequency, laser).

The elongate member or shaft 210 includes a reinforcement layer 260 that may be comprised for example of metal wires spiraled together to form a cylindrical shape To hold the wires in place, the reinforcement layer 260 may include a first weld, solder joint, adhesive, or other joint 270 at or near the proximal end 225, and a second weld, solder joint, adhesive, or other joint 270 at or near the distal end 245, to bond the wires together. In some embodiments, additional welds or joins may be present along the length of the reinforcement layer 260, or may be continuous along the length of the reinforcement layer 260.

In the case of subintimal insertion, the device 200 may be accidentally or deliberately inserted into a space formed between the intima and media of the vessel wall. This may occur for example at the cap of a calcified inclusion, where the resistance of the true lumen may be greater than the resistance provided by pushing to separate the intima of the vessel wall from the media of the vessel wall, thus forming a pseudo-lumen between the intima and media of the vessel wall. In such cases, it is desirable for the distal end 245 of the device 200 to re-enter the true lumen once the distal end 245 is past the occlusion. In order to facilitate re-entry of the distal end 245 into the true lumen of the vessel, the device 200 may include a re-entry needle 280 disposed near the distal end 245. The re-entry needle may be operable such that during normal use of the device 200 the re-entry needle 280 lies within or flush against the elongate body or shaft 210, but during subintimal travel, when the clinician decides to bring the distal end 245 of the device 200 back into the true lumen, the elongate body or shaft 210 is rotated until the needle is in a "12 o'clock position" (e.g., facing the lumen side of the vessel wall), and the re-entry needle 280 is actuated such that it extends away from the body or shaft 210 as shown in FIG. 2, with the result that it punctures the intima, forming an aperture from the subintimal pseudo-lumen into the true lumen. In some embodiments, the re-entry needle 280 may be hollow, such that a guidewire may be passed through it into the true lumen. Once the aperture is formed, the re-entry needle 280 may be retracted back against or into the elongate body or shaft 210 of the device 200, and the distal end 245 of the device 200 may be maneuvered through the aperture and into the true lumen. In an example, the re-entry needle 280 is made of a shape memory alloy such as Nitinol, and is actuated thermally.

With traditional polymer catheters, including catheters that incorporate a wire mesh layer, the success rate of such subintimal insertion and lumen reinsertion maneuvers may be as low as 50%, or lower, due to kinking or buckling of the catheter shaft 210, and/or twisting of the catheter shaft 210, such that there is not 1:1 correspondence between translational or rotational movements of the proximal end 225 and translational or rotational movements of the distal end 245. The present disclosure provides a catheter whose flexibility is comparable to that of a polymer catheter, such that it can readily navigate the tortuous branchings of human vasculature, but which is highly resistant to kinking, buckling, or twisting, such that it maintains 1:1 correspondence in rotational and translational movements.

Figure 3:
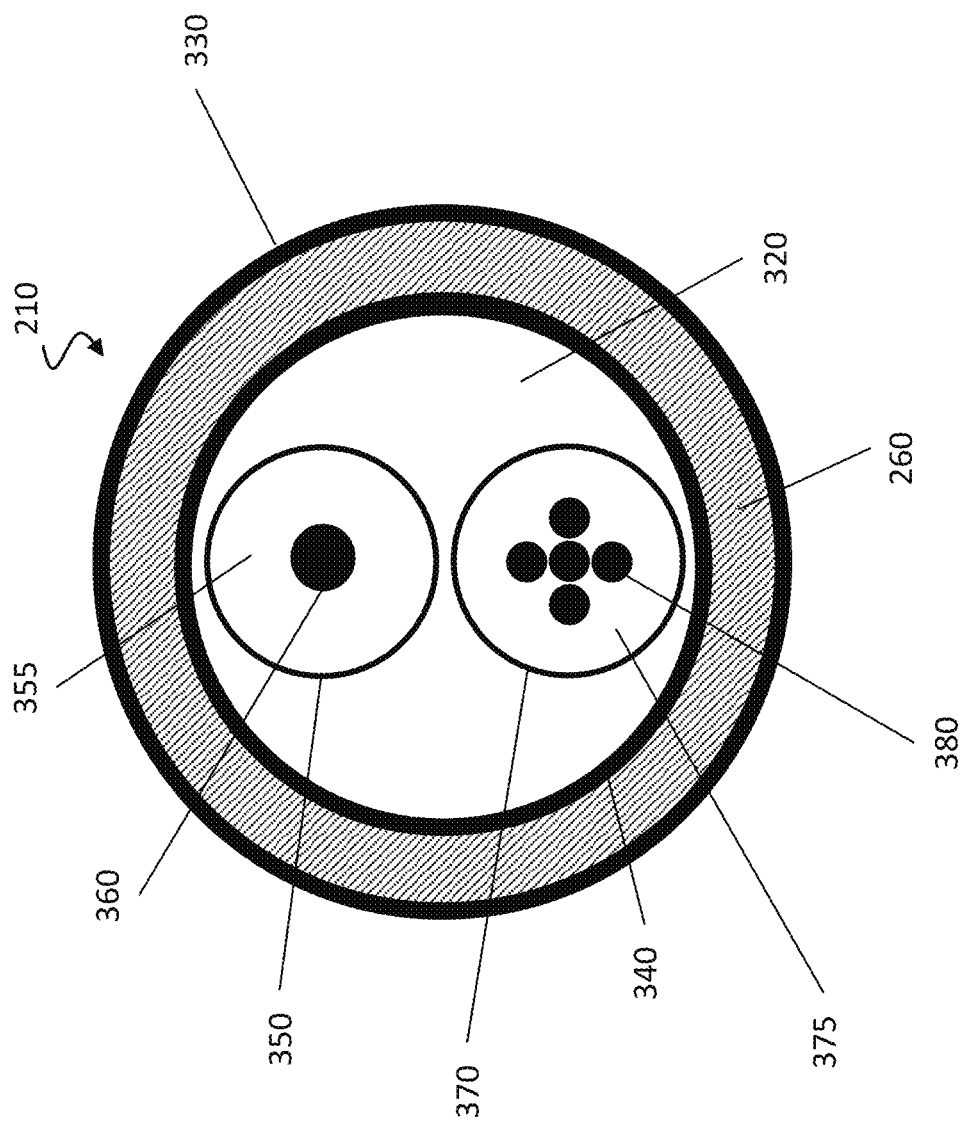
FIG. 3 illustrates a diagrammatic cross-sectional view of the elongate member or shaft of FIG. 2, in accordance with at least one embodiment of the present disclosure.

FIG. 3 illustrates a cross-sectional view of the elongate member or shaft 210 along section lines 2-2 of FIG. 2, in accordance with at least one embodiment of the present disclosure. Referring to FIGS. 2 and 3, the shaft 210 defines the flexible elongate body of the device 200 along the proximal portion 220, central portion 230, and distal portion 240. The shaft 210 defines a central lumen 320, and includes a reinforcement layer 260 (e.g., a layer made of wires spiraled together into a cylinder), and may optionally include an outer layer 330 and/or an inner layer 340. The outer layer 330 and/or the inner layer 340 may for example be made of a polymer material, or may comprise any suitable number of layers of different materials, and may optionally include surface coatings such as hydrophilic or hydrophobic coatings. The polymer material any suitable material, such as Pebax or nylon. The outer layer 330 and inner layer 340 may have the same structure or composition, or may have different structures or compositions. In some embodiments, the wire layer or reinforcement layer 260 may be fully or partially embedded within one or more layers of a polymer material. In some embodiments, the central lumen 320 may be partially or completely filled with a polymer material. In some embodiments, the central lumen 320 may be omitted. The reinforcement layer 260 can surround a solid material and/or an air gap.

In some embodiments, such as when the intravascular device 200 is a catheter, the shaft 210 defines one or more lumens. For example, a main or central lumen 320 may comprise a guidewire tube 350 that defines a guidewire lumen 355 through which a guidewire 360 may pass. Alternatively or in addition, the main lumen 320 may comprise a signal line tube 370 that defines a signal line lumen 375 through which signal lines (e.g., electrical wires, optical fibers, etc.) may pass (e.g., to operate the working element 250 shown in FIG. 2). Other lumens may be included instead of or in addition to those described above, including but not limited to a pullwire lumen that controls deflection of the distal end of the catheter shaft body 210, or a fluid lumen carrying air, gas, or liquid for inflating a balloon. Depending on the implementation, the catheter shaft body 210 may comprise any suitable lumen or lumens as needed, either within the main lumen 320, within the reinforcement layer 260, within the inner layer 340 or outer layer 330, or externally in separate tubes or other structures.

A guide wire, therapy device, and/or other suitable instruments can also be passed through the main lumen 320 of the catheter body or shaft 210. The reinforcement layer 260 of the shaft 210 can be made up of one or more components. For example, aspects of the present disclosure relate to constructing a shaft using multiple metal wires having different sizes and/shapes that are wound together. While a cylindrically shaped shaft 210, with a circular cross-section, is shown, it is understood that the shaft can have any suitable shape.

FIGS. 4-12 illustrate various exemplary aspects of the catheter shaft.

Figure 4:
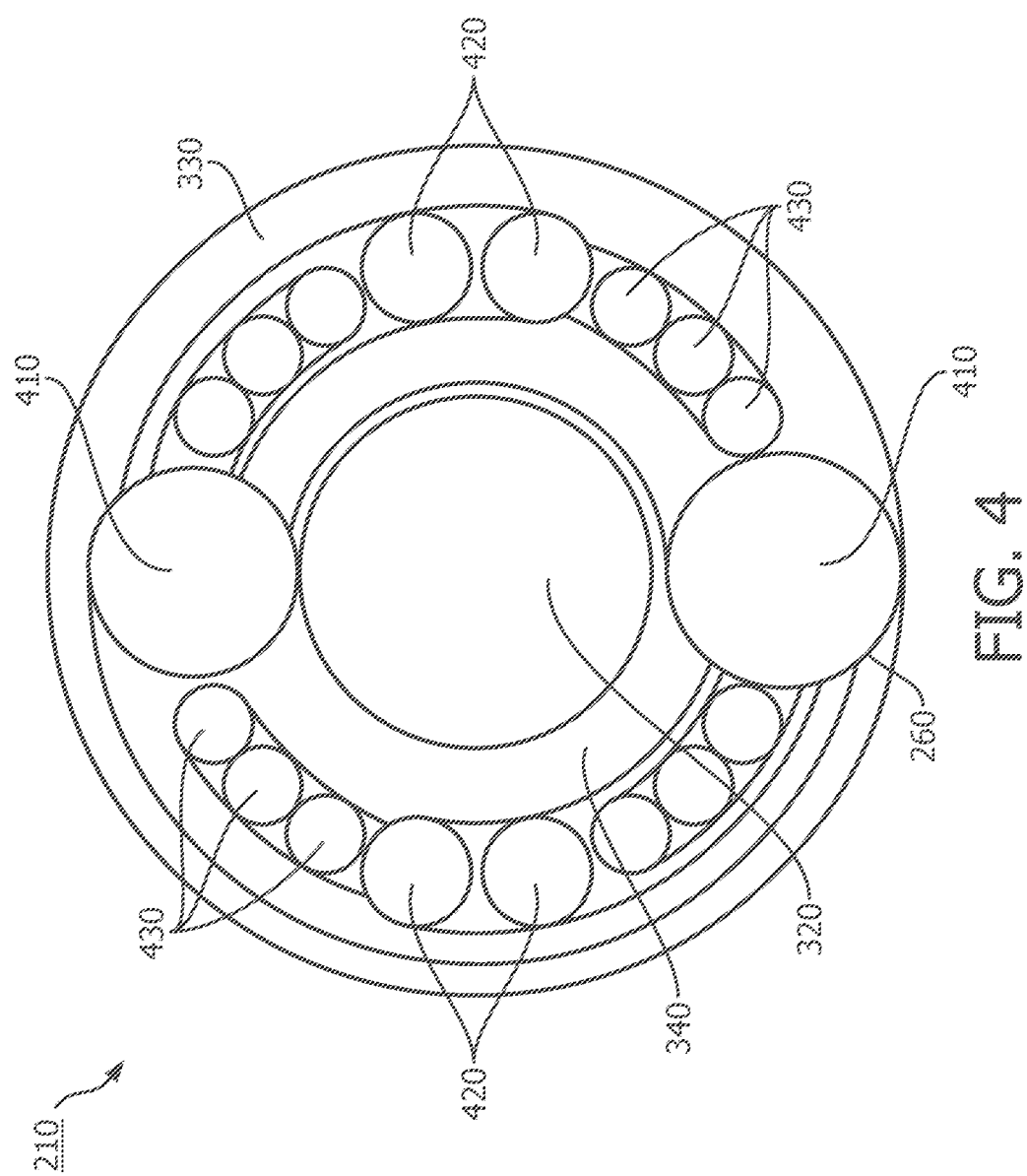
FIG. 4 illustrates a diagrammatic cross-sectional view of an exemplary embodiment of the catheter shaft body, including a reinforcement layer, outer layer, and inner layer, in accordance with at least one embodiment of the present disclosure.

FIG. 4 illustrates a cross-sectional view of exemplary embodiment of the catheter shaft body 210, including a reinforcement layer 260, outer layer 330, and inner layer 340, in accordance with at least one embodiment of the present disclosure. In the example shown in the figure, the reinforcement layer 260 comprises a plurality of wires 410, 420, and 430. All of the wires in the illustrated embodiment have a circular cross-section, although it should be understood that other cross sections may be used instead or in addition. The arrangement of components can include three different sizes of wires. In the example shown in FIG. 4, the reinforcement layer 260 comprises two large wires 410, four medium wires 420, and 12 small wires 430 that are spiraled together as shown below in FIG. 5. Generally, the catheter shaft will be constructed of multiple sizes and shapes of metal wires that are wound next to each other. According to one aspect, this invention is unique as it has a combination of wires that have different shapes and sizes, which is not found in prior art devices. For example, the wires may be helically wound around a central longitudinal axis of the catheter shaft. The shape of the metal wires can be round, ellipse, flat (ribbon), square, pentagon, hexagon, octagon, decagon, dodecagon, triangle, diamond shaped, etc. The wires can be a mix of multiple different sizes (width, thickness, length, etc.). The material of the wires can be any suitable type, including any types of stainless steel, Nitinol, titanium, any form of steels, precious metals, rare metals, ceramics, composites, etc. One, some, or all of the wires forming the reinforcement layer 260 can be radiopaque, such that the intraluminal device is visualized in an x-ray image obtained by, e.g., the external imaging system 132. Wires made of different materials may be combined to form the reinforcement layer 260. In some embodiments, the shaft 210 includes wires of multiple different materials. In other embodiments, wires of the shaft are the same material, though the wires may be different sizes and/or shapes. The metals of one or more wires can be heat treated (e.g., full hard temper) to increase the strength of the component, and/or annealed to provide characteristics as needed. One or more portions of the shaft (e.g., proximal, central, and distal portions) can have heat treatments and/or mix/combine with other types of metal, ceramics, or thermoplastics (cross-linked and/or non-cross linked) to promote different performances such as flexibility, pushability, etc. One or more portions of the shaft 210 (e.g., proximal, central, and distal portions) can be welded together, and may be machined (e.g., with centerless grinding) to have a seamless transition.

Figure 5:
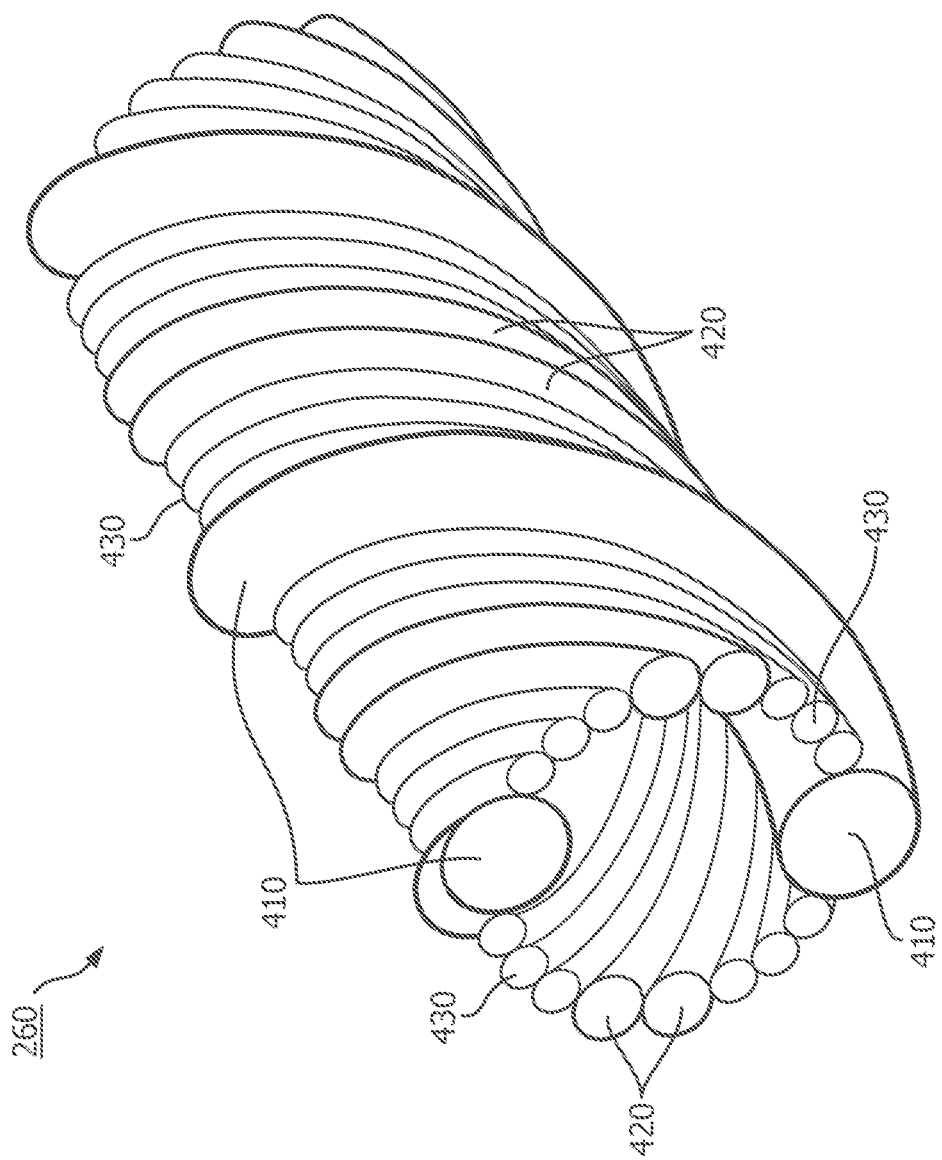
FIG. 5 is a diagrammatic perspective view of the exemplary reinforcement layer of the catheter shaft body shown in FIG. 4, in accordance with at least one embodiment of the present disclosure.

As seen in FIG. 5, where wires of different sizes or shapes are employed, the inner and/or outer diameter or profile of the reinforcement layer 260 may not be constant along its length.

Generally, the catheter shaft 210 can have any suitable diameter. For example, the catheter shaft may be between 1 Fr-15 Fr, and other suitable sizes, both larger and smaller. In some embodiment, the diameter of the shaft can vary along the proximal, central, and distal portions. Individual wires that are wound together to form the catheter shaft can have a diameter between, e.g., 0.0002 mm and 1.3 mm, and other suitable sizes, both larger and smaller.

The shaft 210 of FIGS. 3 and 4 can also include one or more inner and/or outer plastic and/or polymer layers (e.g., layers 330 and 340). For example, the wound wires are sandwiched between the plastic/polymer layers. The inner and/or outer plastic/polymer layer can provide a constant and/or smooth inner and/or outer diameter even though individual wires of varying diameter or cross-sectional area are used.

FIG. 5 is a perspective view of the exemplary reinforcement layer 260 of a catheter shaft body 210 shown in FIG. 4, in accordance with at least one embodiment of the present disclosure. Visible are the large wires 410, medium wires 420, and small wires 430. The wires are wound or spiraled together with a certain rotational pitch, e.g., a certain distance to complete a full revolution. In an example, a pitch of infinity indicates that the wires are straight (e.g., needles). This may be correlated with high pushability, but also high stiffness and low flexibility. Conversely, a very small pitch (e.g., 3 mm) may be correlated with modest pushability and 1:1 correlation in translational and rotational movements, but substantially greater flexibility. Accordingly, it may be desirable to adjust the flexibility of the reinforcement layer 260 to a desired value, by adjusting the rotational pitch of the wires.

The catheter shaft can have different stiffness across different sections/segments of entire catheter length. For example, proximal portion, central portion, and/or distal portion (as shown for example in FIG. 2) can have different stiffnesses. In some embodiments, the distal portion can have greater flexibility than the central and proximal portions, the central portion can have a flexibility greater than the proximal section but less than the distal portion, and the proximal portion can have a flexibility less than the central or distal portions. In such embodiments, the construction of the shaft in the distal, central, and/or proximal portions can be different to provide the varying flexibility. In other embodiments, the construction of the shaft along the distal, central, and/or proximal portions can be the same.

In the exemplary embodiment shown in FIG. 5, the wires are wound together such that the two large size wires 410 are disposed opposite one another. Pairs of medium-sized wires 420 are disposed opposite one another. Two medium sized wires 420 are adjacent to one another. Groupings of three small size wires 430 are positioned between the large size wire and the pair of medium size wires. Three small sizes wires 430 are adjacent to one another. A small size wire 430 can be adjacent to a large size wire 410. A small size wire 430 can be adjacent to a medium sized wire 420. Because of the varying diameters of the individual wires, the inner and outer diameter of the reinforcement layer is not constant, but varies according diameter of the individual wires.

In general, larger wires provide a greater stiffness and pushing force, but require a larger diameter and/or a smaller lumen for the catheter. Smaller wires provide less pushing force, but allow for greater flexibility, along with a smaller outer diameter and/or a larger lumen diameter for the catheter. A mixture of larger and smaller wires (e.g., wires with larger and smaller diameters or cross-sectional areas) may thus provide a good overall compromise between push force, catheter diameter, lumen diameter, and flexibility. Wires woven into a diamond pattern (e.g., extending in two opposite directions and interleaved or woven) may tend to open up (e.g., bulge) when compressed, whereas wires spiraled helically in a single direction or chirality are less prone to this behavior, and can thus withstand greater longitudinal pressure or force.

Figure 6:
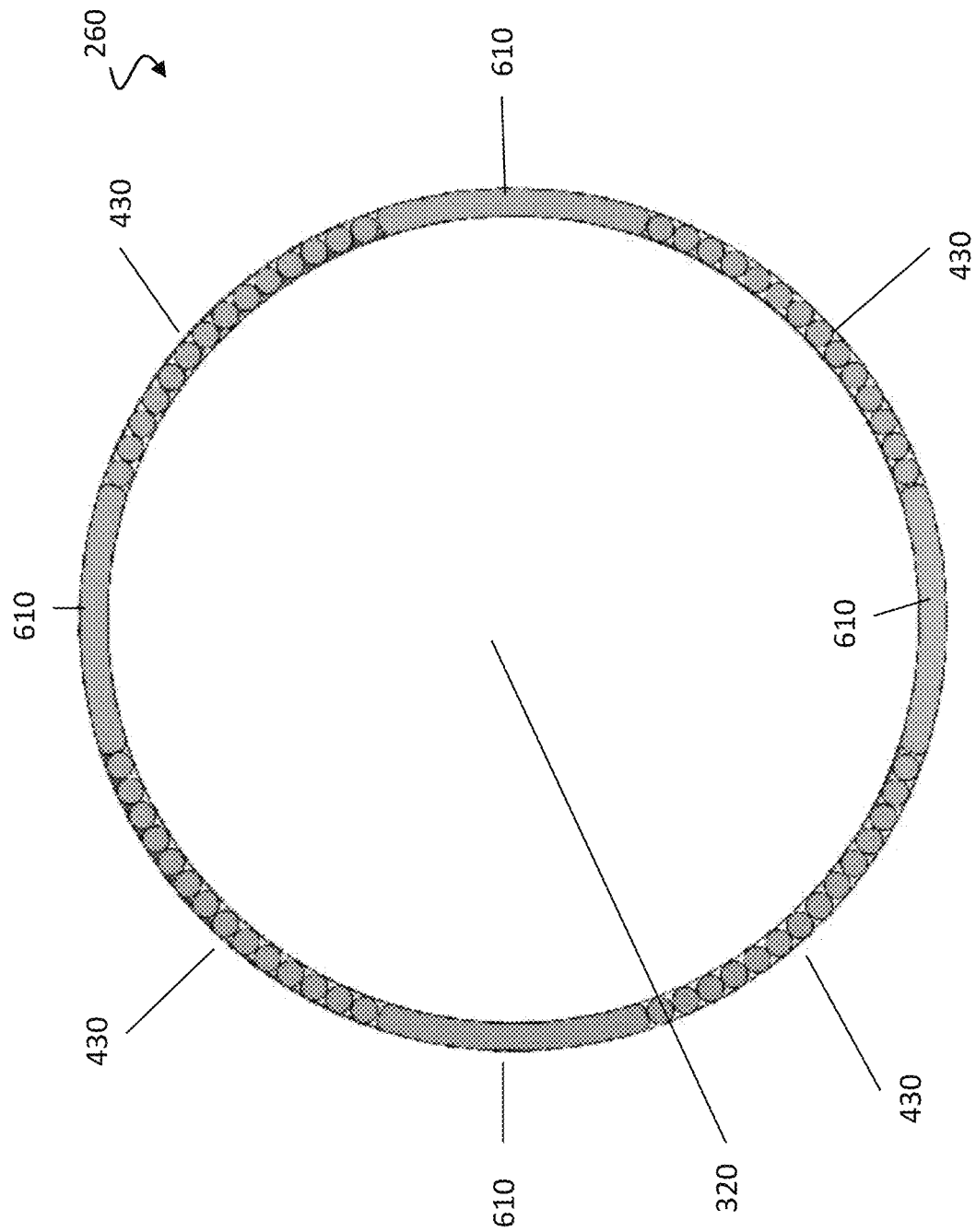
FIG. 6 is a diagrammatic cross-sectional view of an exemplary construction of the reinforcement layer, in accordance with at least one embodiment of the present disclosure.

FIG. 6 is a cross-sectional view of an exemplary construction of the reinforcement layer 260, in accordance with at least one embodiment of the present disclosure. The wires in the illustrated embodiment have different shapes and sizes. For example, arrangement of components in FIG. 6 includes four larger ribbon or flat-shaped wires 610, and four groupings of small sized wires 430 with a circular cross-section (e.g., a plurality of wires totaling between 4 and 80 wires, and/or other suitable amounts, both larger and smaller). Any suitable number of larger wires 610 can be used, such as between 2 and 20 wires and/or other suitable amounts both larger and smaller. The ribbon wires 610 have cross-section that is approximately rectangular, but curved to conform with the circumference of the reinforcement layer 260. Individual groupings of small wires 430 (e.g., between 1 and 20 wires, and/or other suitable amounts) are disposed between individual ribbon or flat-shaped wires 610. In different embodiments, groupings of wires can have the same or different number of individual wires. In this example, the four ribbon or flat-shaped wires 610 are evenly spaced around the circumference, and each group of smaller wires 430 is evenly spaced around the circumference.

In general, ribbon-shaped wires are stiffer than groups of small circular wires having a similar overall cross-sectional area. Thus, the arrangement shown in FIG. 6 provides some of the stiffness and push force advantages of FIGS. 4 and 5, while simultaneously permitting a smaller diameter for the reinforcement layer 260, a larger diameter for the lumen 320, and a smoother overall profile.

Figure 7:
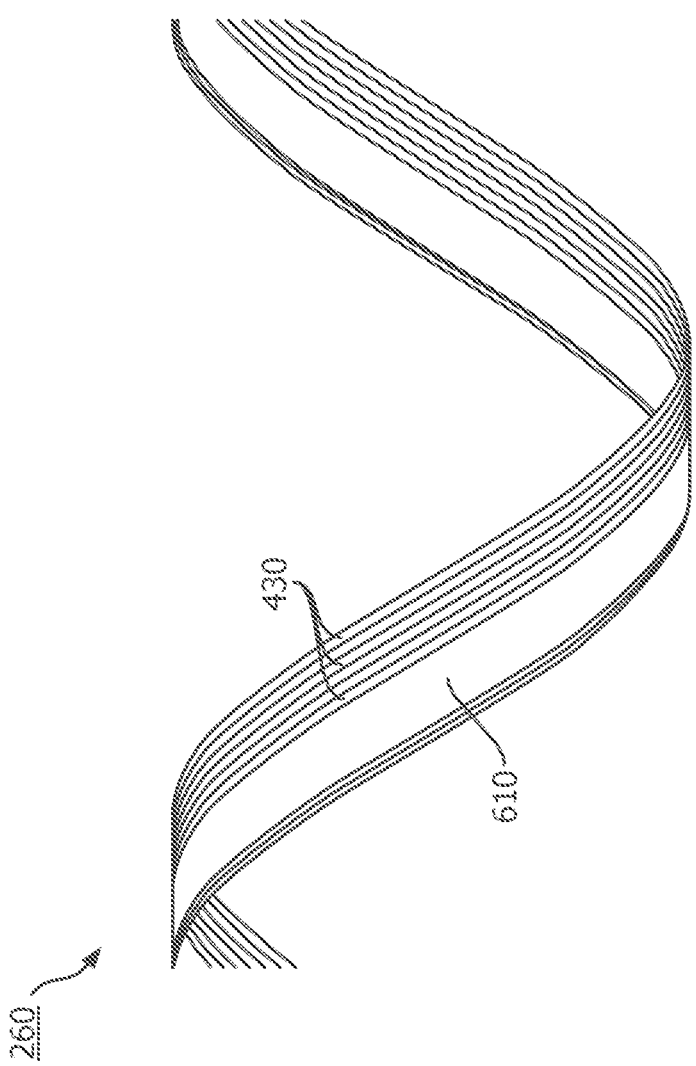
FIG. 7 is a diagrammatic side view of an exemplary construction of a portion of the reinforcement layer, in accordance with at least one embodiment of the present disclosure.

FIG. 7 is a side view of an exemplary construction of a portion of the reinforcement layer 260, in accordance with at least one embodiment of the present disclosure. The wires in the illustrated embodiment have different shapes and sizes. For example, FIG. 7 shows one larger ribbon or flat-shaped wire 610 adjacent to one group of small sized wires 430. Wires of different sizes and/or shapes can be helically wound or twisted together.

Figure 8:
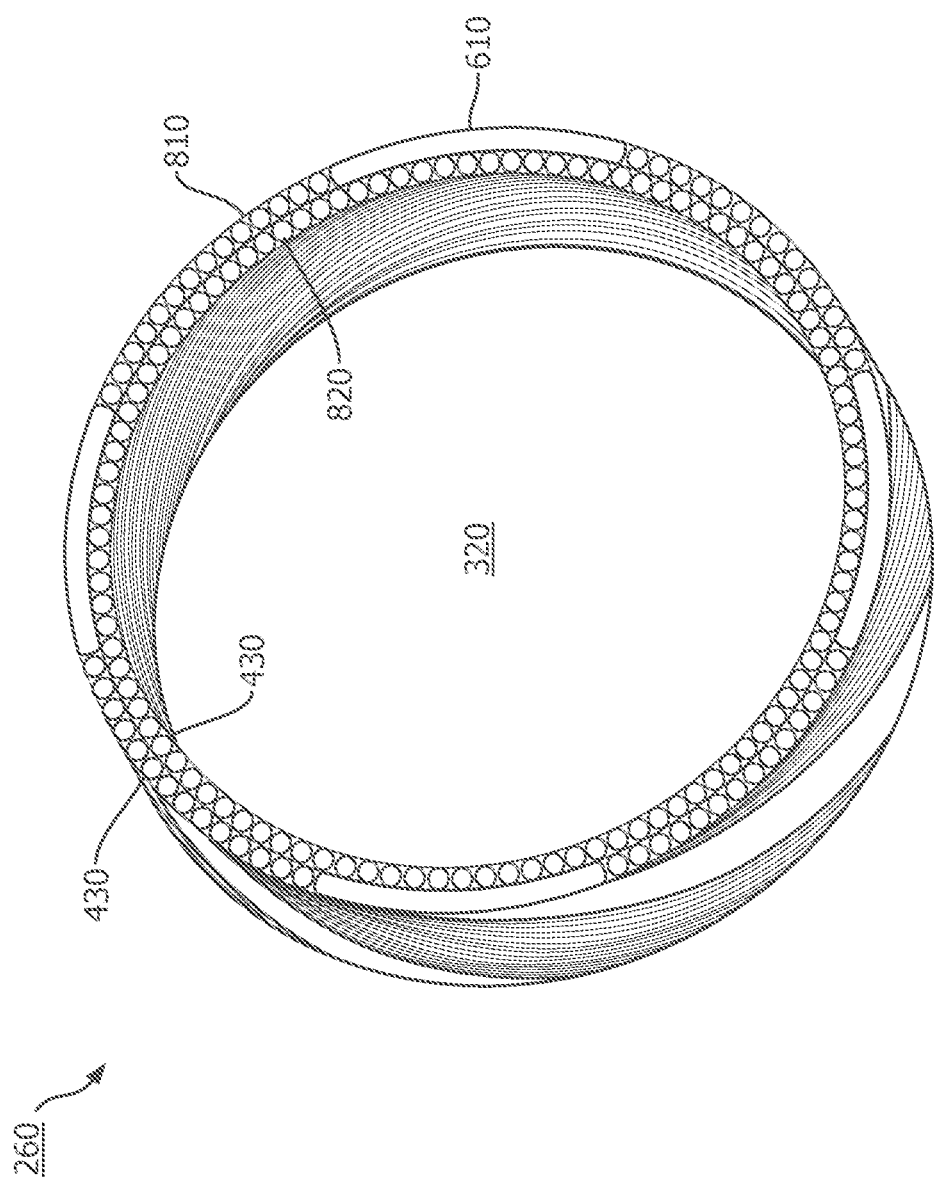
FIG. 8 is a diagrammatic perspective view of an exemplary construction of a portion of the reinforcement layer, in accordance with at least one embodiment of the present disclosure.

FIG. 8 is a perspective view of an exemplary construction of a portion of the reinforcement layer 260, in accordance with at least one embodiment of the present disclosure. The illustrated embodiment includes two layers of wires: an outer wire layer 810 and an inner wire layer 820. The outer wire layer 810 is radially adjacent to the inner wire layer 820. While two layers of wires are shown, it should be understood that one, two, three, four, or more layers of wires could be employed. Layers 810 and 820, or additional layers, may be wound in opposite directions or in the same direction. In some instances, the wires of the layer 810 can be referenced as a first plurality of wires and the wires of the layer 820 can be referenced as a second plurality of wires. In the pictured embodiment, each layer has a different construction. For example, the inner wire layer 820 includes a plurality of wires 430 that have the same size and shape. As shown, the inner wire layer 820 includes a plurality of small wires 430, each with a circular cross-section (e.g., between 20 and 200 wires, and other suitable amounts, both larger and smaller). The outer layer includes wires having different shapes and sizes. The outer layer of FIG. 8 is similar to the single layer of FIG. 6.

In some embodiments, the plurality of wires of the reinforcement layer 260 are not a mesh or a braid. For example, the wires of the layer 810 are not interwoven with the wires of the layer 820 such that the wires cross over and under one another. Rather, the wires of the layer 810 are helically twisted such that these wires alone form the layer 810. Similarly, the wires of the layer 820 are helically twisted such that these wires alone form the layer 820. The size, shape, quantity, and/or pitch of the wires, as well as how the wires are joined at the proximal and/or distal end of the intraluminal device, allow for the wires in a given layer to define the perimeter of that layer. The wires in a given layer are adjacent to one another. The wires in a given layer are twisted such that each has the same or similar helical shape relative to an adjacent wire. The similar helical shapes are offset from one another in a longitudinal direction such that the wires fit together to form a given layer.

Figure 9:
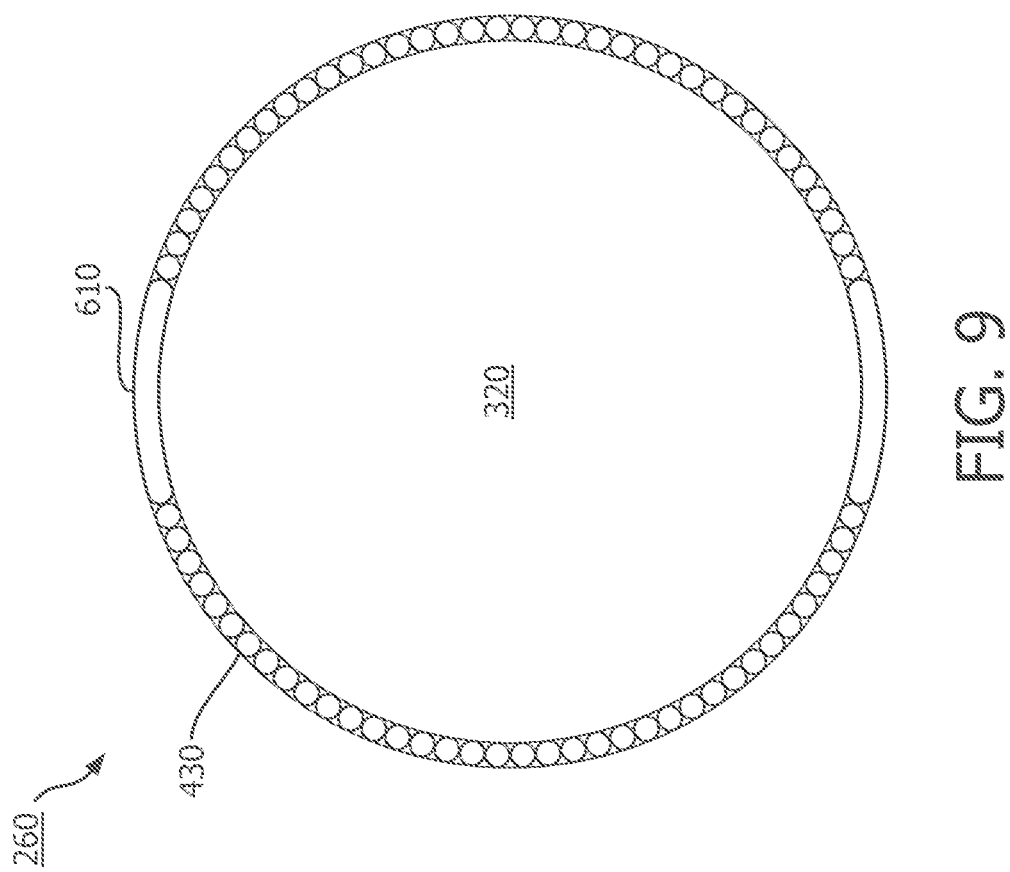
FIG. 9 is a diagrammatic cross-sectional view of an exemplary construction of the reinforcement layer, in accordance with at least one embodiment of the present disclosure.

FIG. 9 is a cross-sectional view of an exemplary construction of the reinforcement layer 260, in accordance with at least one embodiment of the present disclosure. The wires in the illustrated embodiment have different shapes and sizes. For example, arrangement of components in FIG. 9 includes two larger ribbon or flat-shaped wires 610 and two grouping of small sized wires 430 with a circular cross section (e.g., a plurality of wires totaling between 20 and 80 wires, and other suitable amounts, both larger and smaller). Individual grouping of small wires 430 (e.g., 10-50 wires, and other suitable amounts, both larger and smaller) are disposed between individual ribbon or flat-shaped wires 610. The two ribbon or flat-shaped wires 610 are disposed opposite one another around the circumference. The two grouping of smaller wires 430 are disposed opposite one another around the circumference.

Figure 10:
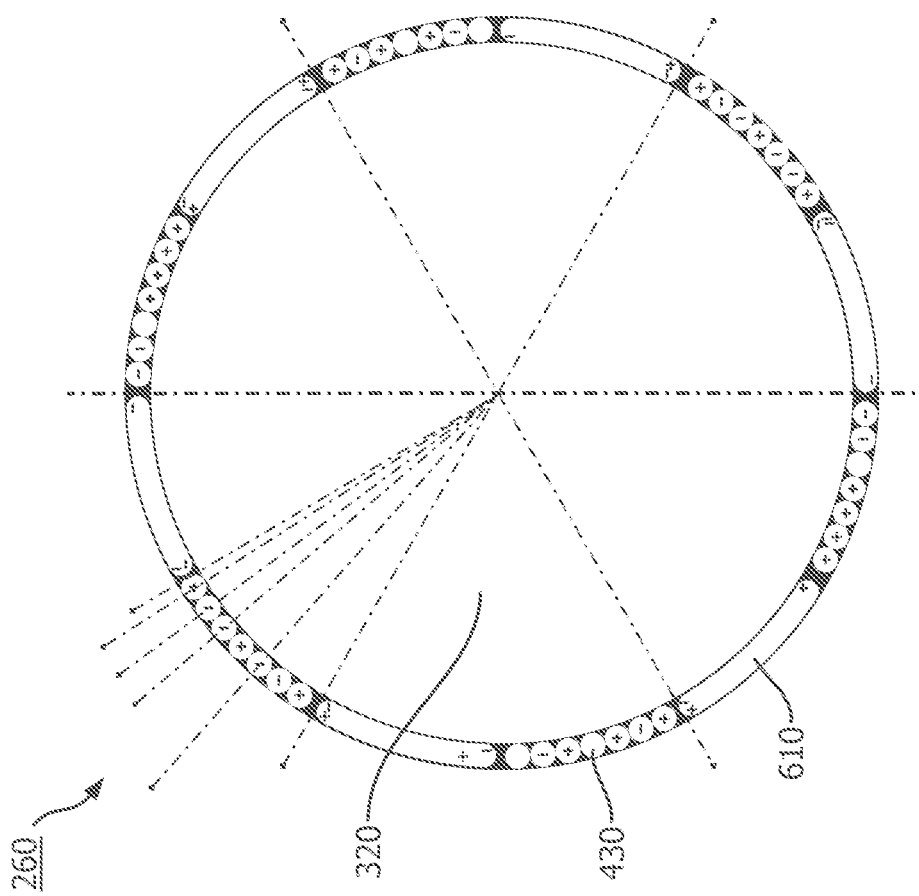
FIG. 10 is a diagrammatic cross-sectional view of an exemplary construction of the reinforcement layer, in accordance with at least one embodiment of the present disclosure.

FIG. 10 is a cross-sectional view of an exemplary construction of the reinforcement layer 260, in accordance with at least one embodiment of the present disclosure. The wires in the illustrated embodiment have different shapes and sizes. For example, arrangement of components in FIG. 10 includes six larger ribbon or flat-shaped wires 610 and six groupings of small sized wires 430 with a circular cross-section (e.g., a plurality of wires totaling between 20 and 60 wires, and other suitable amounts, both larger and smaller). Individual groupings of small wires 430 (e.g., 3-10 wires, and other suitable amounts, both larger and smaller) are respectively disposed between individual ribbon or flat-shaped wires 610. The six ribbon or flat-shaped wires 610 are evenly spaced around the circumference. Each group of smaller wires 430 is evenly spaced around the circumference.

Figure 11:
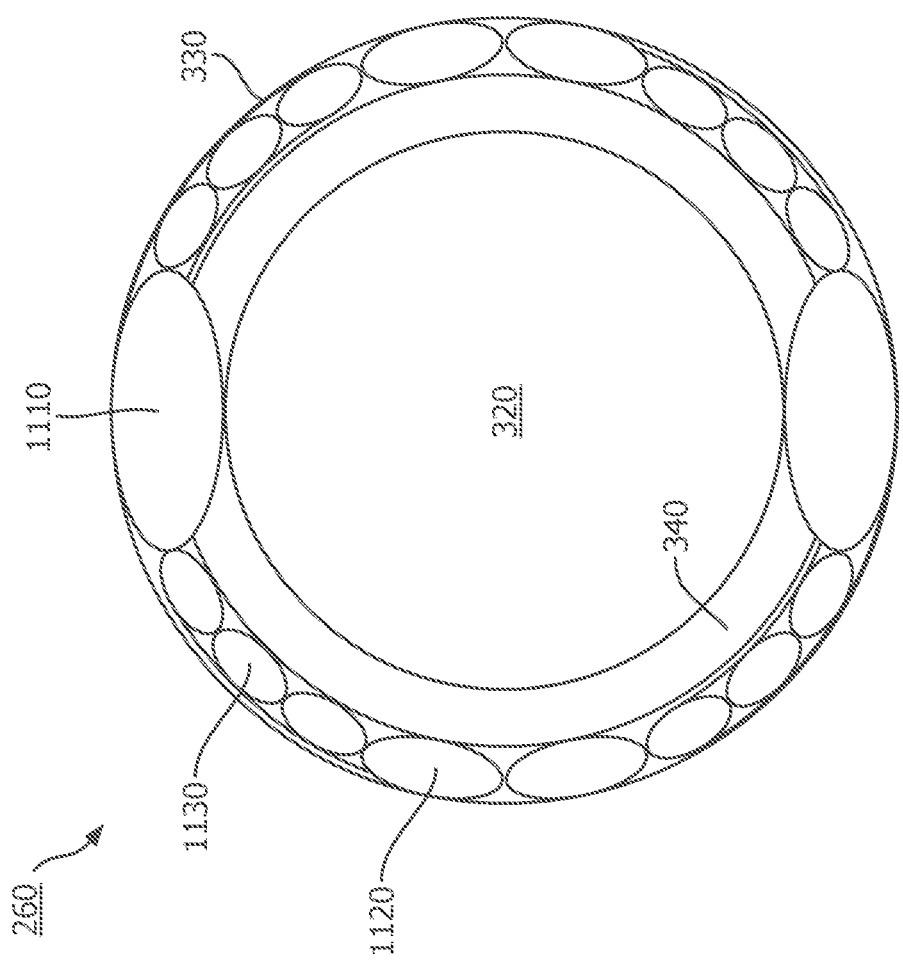
FIG. 11 is a diagrammatic cross-sectional view of an exemplary construction the reinforcement layer, in accordance with at least one embodiment of the present disclosure.

FIG. 11 is a cross-sectional view of an exemplary construction the reinforcement layer 260, in accordance with at least one embodiment of the present disclosure. The construction of FIG. 11 is similar to that of FIG. 5, except that the large wires 1110, medium wires 1120, and small wires 1130 have non-circular cross sections. In particular, the large wires 1110, medium wires 1120, and small wires 1130 have oval cross sections whose long axes are arranged around the circumference of the reinforcement layer 260. In that regard, the oval-shaped wires share some aspects in common with both circular wires and flat, ribbon-shaped wires of equivalent cross sectional area, and are thus a compromise between four desirable goals of greater pushing force, greater flexibility, smaller reinforcement layer diameter, and larger lumen diameter.

Also visible are an outer layer 330, inner layer 340, and lumen 320.

Figure 12:
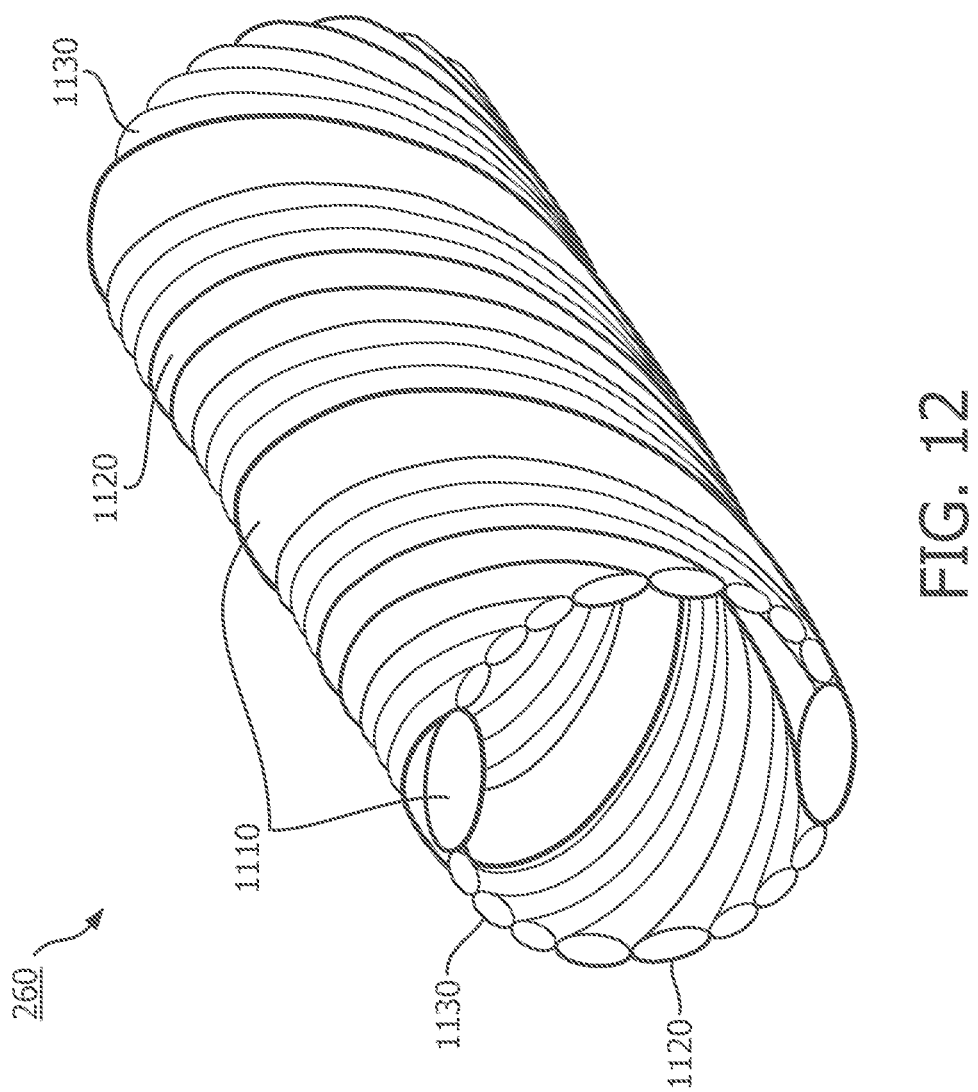
FIG. 12 is a diagrammatic perspective view of the exemplary reinforcement layer of FIG. 11, in accordance with at least one embodiment of the present disclosure

FIG. 12 is a perspective view of the exemplary reinforcement layer 260 of FIG. 11, in accordance with at least one embodiment of the present disclosure. The longitudinal variation in the outer and inner diameters of the reinforcement layer 260 is less pronounced with this embodiment than with the embodiment shown in FIGS. 4 and 5, though more pronounced than shown in FIGS. 6-10.

Accordingly, it can be seen that the catheter shaft body fills a need in the art, by providing a flexible catheter body or shaft that supports large pushing force, without kinking, buckling, bulging, or twisting, and exhibits 1:1 correspondence between translational and rotational movements of its proximal and distal ends.

A number of variations are possible on the examples and embodiments described above. For example, the catheter shaft body may be configured for the treatment of body lumens other than vasculature, including for example the urethra, kidneys, fallopian tubes, and nasal cavities. The technology described herein may be employed in veterinary medicine as well as human medicine, and can be used in any setting (whether medical or nonmedical) where a catheter must be pushed against substantial resistance without buckling, kinking, bulging, or twisting.

The logical operations making up the embodiments of the technology described herein are referred to variously as operations, steps, objects, elements, components, or modules. Furthermore, it should be understood that these may occur or be performed in any order, unless explicitly claimed otherwise or a specific order is inherently necessitated by the claim language.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the catheter shaft body. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the catheter shaft body as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intraluminal catheter, comprising:
 a flexible elongate shaft configured to be positioned within a body lumen of a patient, wherein the flexible elongate shaft comprises a proximal portion and a distal portion;
 an intraluminal imaging sensor disposed at the distal portion and configured to obtain an intraluminal ultrasound image of the body lumen or an optical coherence tomography (OCT) image of the body lumen while positioned within the body lumen;
 one or more signal lines coupled to the intraluminal imaging sensor,
 wherein the flexible elongate shaft further comprises a plurality of helically twisted wires,
 wherein each wire of the plurality of helically twisted wires is only circumferentially adjacent to a nearest wire of the plurality of helically twisted wires such that the plurality of twisted wires defines a lumen sized and shaped to accommodate a guidewire and the one or more signal lines,
 wherein all of the plurality of helically twisted wires are twisted in the same direction along a length of the flexible elongate shaft between the proximal portion and the distal portion such that the plurality of helically twisted wires is not a braid,
 wherein the plurality of helically twisted wires is stationary in relation to the flexible elongate shaft,
 wherein each wire of the plurality of helically twisted wires is directly adjacent to another wire of the plurality of helically twisted wires such that the plurality of helically twisted wires cover the length without an opening.

2. The intraluminal catheter of claim 1, wherein the plurality of helically twisted wires extends from the proximal portion of the flexible elongate shaft to the distal portion of the flexible elongate shaft.

3. The intraluminal catheter of claim 1, wherein the plurality of helically twisted wires comprises a proximal portion and a distal portion, wherein a cylindrical shape is open at the proximal portion of the plurality of helically twisted wires and the distal portion of the plurality of helically twisted wires.

4. The intraluminal catheter of claim 1, wherein the plurality of helically twisted wires comprises a proximal portion and a distal portion, wherein the plurality of helically twisted wires is coupled only at the proximal portion of the plurality of helically twisted wires and the distal portion of the plurality of helically twisted wires.

5. The intraluminal catheter of claim 1, wherein the flexible elongate shaft further comprises a plurality of lumens, wherein the plurality of helically twisted wires is disposed around the plurality of lumens.

6. The intraluminal catheter of claim 1, wherein the plurality of helically twisted wires comprises a pitch associated with the helical twist, wherein a larger pitch corresponds to an increased stiffness and decreased flexibility of the flexible elongate shaft and a smaller pitch corresponds to a decreased stiffness and increased flexibility of the flexible elongate shaft.

7. The intraluminal catheter of claim 1, wherein the plurality of helically twisted wires comprises wires of different sizes and/or wires of different shapes.

8. The intraluminal catheter of claim 7, wherein the plurality of helically twisted wires is adjacent to one another to form a cylindrical shape.

9. The intraluminal catheter of claim 7, wherein the plurality of helically twisted wires comprises wires of different cross-sectional areas and/or wires of different cross-sectional shapes.

10. The intraluminal catheter of claim 1, wherein the plurality of helically twisted wires comprises an inner profile and an outer profile, wherein at least one of the inner profile or the outer profile is varying.

11. The intraluminal catheter of claim 1, wherein the plurality of helically twisted wires comprises an inner profile and an outer profile, wherein at least one of the inner profile or the outer profile is constant.

12. The intraluminal catheter of claim 1, wherein the flexible elongate shaft further comprises an inner polymer layer, wherein the plurality of helically twisted wires is positioned around the inner polymer layer.

13. The intraluminal catheter of claim 1, wherein the flexible elongate shaft further comprises an outer polymer layer, wherein the outer polymer layer is positioned around the plurality of helically twisted wires.

14. The intraluminal catheter of claim 1, further comprising a retractable needle disposed at the distal portion of the flexible elongate shaft.

15. The intraluminal catheter of claim 1,
wherein the one or more signal lines extend inside the lumen defined by the helically twisted wires such that signals associated with operation of the intraluminal imaging sensor pass:
inside the lumen defined by the helically twisted wires; and
between the proximal portion and the intraluminal imaging sensor at the distal portion.

16. An intravascular catheter, comprising:
a flexible elongate shaft configured to be positioned within a blood vessel of a patient, wherein the flexible elongate shaft comprises a proximal portion and a distal portion;
an intravascular imaging sensor disposed at the distal portion and configured to obtain an intravascular image of the blood vessel while positioned within the blood vessel, wherein the intravascular imaging sensor comprises an intravascular ultrasound (NUS) transducer or an optical coherence tomography (OCT) device;
one or more signal lines coupled to the intraluminal imaging sensor,
wherein the flexible elongate shaft further comprises a plurality of helically twisted wires,
wherein each wire of the plurality of helically twisted wires is only circumferentially adjacent to a nearest wire of the plurality of helically twisted wires such that the plurality of twisted wires defines a lumen sized and shaped to accommodate a guidewire and the one or more signal lines,
wherein the plurality of helically twisted wires extends along a length from the proximal portion of the flexible elongate shaft to the distal portion of the flexible elongate shaft,
wherein the plurality of helically twisted wires is stationary in relation to the flexible elongate shaft,
wherein all of the plurality of helically twisted wires are twisted in a single direction to form a cylindrical shape such that the plurality of helically twisted wires is not a braid and covers the length without an opening,
wherein the plurality of helically twisted wires form the cylindrical shape, and
wherein the plurality of the helically twisted wires is configured to stiffen the flexible elongate member for movement into an obstruction within the blood vessel without kinking.

17. The intravascular catheter of claim 16, wherein the plurality of helically twisted wires comprises wires of different cross-sectional areas and/or wires of different cross-sectional shapes.

* * * * *